(12) United States Patent
Birikh et al.

(10) Patent No.: US 10,815,471 B2
(45) Date of Patent: Oct. 27, 2020

(54) METHOD FOR PRODUCING REDUCING SUGAR FROM LIGNOCELLULOSIC SUBSTRATES

(71) Applicant: Metgen OY, Kaarina (FI)

(72) Inventors: Klara Birikh, Kaarina (FI); Antoine Patrice Noel Mialon, Kaarina (FI); Matti Wilhelm Heikkila, Kaarina (FI); Anu Minna Maaret Suonpaa, Kaarina (FI)

(73) Assignee: MetGen Oy, Kaarina (FI)

( * ) Notice: Subject to any disclaimer, the term of this patent is extended or adjusted under 35 U.S.C. 154(b) by 32 days.

(21) Appl. No.: 16/062,583

(22) PCT Filed: Dec. 8, 2016

(86) PCT No.: PCT/EP2016/080253
§ 371 (c)(1),
(2) Date: Jun. 14, 2018

(87) PCT Pub. No.: WO2017/102540
PCT Pub. Date: Jun. 22, 2017

(65) Prior Publication Data
US 2018/0355342 A1    Dec. 13, 2018

(30) Foreign Application Priority Data
Dec. 15, 2015 (EP) ..................... 15200247

(51) Int. Cl.
*C12N 9/88* (2006.01)
*C12P 19/02* (2006.01)
*C12P 19/14* (2006.01)

(52) U.S. Cl.
CPC .............. *C12N 9/88* (2013.01); *C12P 19/02* (2013.01); *C12P 19/14* (2013.01); *C12Y 402/02002* (2013.01)

(58) Field of Classification Search
None
See application file for complete search history.

(56) References Cited

FOREIGN PATENT DOCUMENTS

| WO | 2008138109 | 11/2008 |
|---|---|---|
| WO | 2010000858 | 1/2010 |
| WO | 2014146713 | 9/2014 |

OTHER PUBLICATIONS

Qui et al., "Enhanced the enzymatic hydrolysis efficiency of wheat straw after combined steam explosion and laccase pretreatment", Bioresource Technology, 2012, vol. 118, pp. 8-12. dx.doi.org/10.1016/j.biortech.2012.05.033.*
International Search Report and Written Opinion for International Application No. PCT/EP2016/080265, dated Feb. 27, 2017, 12 pgs.
Massiot et al., "Enzymic Analysis of Carrot Cell-Wall Polysaccharides," Elsevier Science Publishers, Oct. 11, 1989, pp. 121-136.
Takao et al., "Purification and Characterization of Thermostable Pectate Lyase with Protopectinase Activity from Thermophilic Bacillus," Department of Food Science and Nutrition, May 8, 2000, pp. 2362-2367.
PCT International Search Report and Written Opinion for International Application No. PCT/EP2016/080253, dated Feb. 27, 2017, 10 pgs.

* cited by examiner

*Primary Examiner* — Suzanne M Noakes
(74) *Attorney, Agent, or Firm* — Patent Law Works, LLP

(57) ABSTRACT

The invention relates to processes for the conversion of biomass into carbohydrates, notably reducing sugars. It provides means and methods for increasing the yield of enzymatic digestion of a biomass, in particular in methods wherein cellulose is converted into sugars using a cellulose-converting enzyme. More in particular, the invention provides a method for producing a reducing sugar from a lignocellulosic material, wherein the lignocellulosic material is contacted with a pectate lyase at a pH between 9 and 12, wherein the pectate lyase comprises an amino acid sequence according to SEQ ID NO: 1 or an amino acid sequence at least 70% identical with SEQ ID NO: 1.

12 Claims, No Drawings

Specification includes a Sequence Listing.

SEQUENCE LISTING

<160> NUMBER OF SEQ ID NOS: 8

<210> SEQ ID NO 1
<211> LENGTH: 416
<212> TYPE: PRT
<213> ORGANISM: Bacillus spec.

<400> SEQUENCE: 1

Lys Glu Leu Gly His Glu Val Leu Lys Pro Tyr Asp Gly Trp Ala Ala
1               5                   10                  15

Tyr Gly Glu Gly Thr Thr Gly Gly Ala Met Ala Ser Pro Gln Asn Val
            20                  25                  30

Phe Val Val Thr Asn Arg Thr Glu Leu Ile Gln Ala Leu Gly Gly Asn
        35                  40                  45

Asn His Thr Asn Gln Tyr Asn Ser Val Pro Lys Ile Ile Tyr Val Lys

```
                     50                  55                  60
Gly Thr Ile Asp Leu Asn Val Asp Asp Asn Asn Gln Pro Val Gly Pro
 65                      70                  75                  80

Asp Phe Tyr Lys Asp Pro His Phe Asp Phe Glu Ala Tyr Leu Arg Glu
                 85                  90                  95

Tyr Asp Pro Ala Thr Trp Gly Lys Lys Glu Val Glu Gly Pro Leu Glu
            100                 105                 110

Glu Ala Arg Val Arg Ser Gln Lys Lys Gln Lys Asp Arg Ile Met Val
        115                 120                 125

Tyr Val Gly Ser Asn Thr Ser Ile Ile Gly Val Gly Lys Asp Ala Lys
    130                 135                 140

Ile Lys Gly Gly Gly Phe Leu Ile Lys Asn Val Asp Asn Val Ile Ile
145                 150                 155                 160

Arg Asn Ile Glu Phe Glu Ala Pro Leu Asp Tyr Phe Pro Glu Trp Asp
                165                 170                 175

Pro Thr Asp Gly Thr Leu Gly Glu Trp Asn Ser Glu Tyr Asp Ser Ile
            180                 185                 190

Ser Ile Glu Gly Ser Ser His Ile Trp Ile Asp His Asn Thr Phe Thr
        195                 200                 205

Asp Gly Asp His Pro Asp Arg Ser Leu Gly Thr Tyr Phe Gly Arg Pro
    210                 215                 220

Phe Gln Gln His Asp Gly Ala Leu Asp Ile Lys Asn Ser Ser Asp Phe
225                 230                 235                 240

Ile Thr Ile Ser Tyr Asn Val Phe Thr Asn His Asp Lys Val Thr Leu
                245                 250                 255

Ile Gly Ala Ser Asp Ser Arg Met Ala Asp Ser Gly His Leu Arg Val
            260                 265                 270

Thr Leu His His Asn Tyr Lys Asn Val Thr Gln Arg Leu Pro Arg
        275                 280                 285

Val Arg Phe Gly Gln Val His Ile Tyr Asn Asn Tyr Glu Phe Ser
    290                 295                 300

Asn Leu Ala Asp Tyr Asp Phe Gln Tyr Ala Trp Gly Val Gly Val Phe
305                 310                 315                 320

Ser Gln Ile Tyr Ala Gln Asn Asn Tyr Phe Ser Phe Asp Trp Asp Ile
                325                 330                 335

Asp Pro Ser Leu Ile Ile Lys Val Trp Ser Lys Asn Glu Glu Ser Met
            340                 345                 350

Tyr Glu Thr Gly Thr Ile Val Asp Leu Pro Asn Gly Arg Arg Tyr Ile
        355                 360                 365

Asp Leu Val Ala Ser Tyr Asn Glu Ser Asn Thr Leu Gln Leu Lys Lys
    370                 375                 380

Glu Val Thr Trp Lys Pro Met Phe Tyr His Val Ile His Pro Thr Pro
385                 390                 395                 400

Ser Val Pro Ala Leu Val Lys Ala Lys Ala Gly Ala Gly Asn Leu His
                405                 410                 415

<210> SEQ ID NO 2
<211> LENGTH: 416
<212> TYPE: PRT
<213> ORGANISM: Bacillus spec.

<400> SEQUENCE: 2

Lys Glu Leu Gly His Asp Val Leu Lys Pro Tyr Asp Gly Trp Ala Ser
  1               5                  10                  15
```

Tyr Gly Glu Gly Thr Thr Gly Gly Ser Met Ala Ser Pro Gln Asn Val
                    20                  25                  30

Tyr Thr Val Thr Asn Lys Thr Glu Leu Val Gln Ala Leu Gly Gly Asn
                35                  40                  45

Asn His Thr Asn Gln Tyr Asn Ser Val Pro Lys Ile Ile Tyr Val Lys
            50                  55                  60

Gly Thr Ile Glu Leu Asn Val Asp Asp Asn Asn Gln Pro Val Gly Pro
65                  70                  75                  80

Glu Phe Tyr Lys Asp Pro His Tyr Asp Phe Glu Ala Tyr Leu Lys Glu
                85                  90                  95

Tyr Asp Pro Lys Lys Trp Gly Lys Lys Glu Val Ser Gly Pro Leu Glu
                100                 105                 110

Glu Ala Arg Ala Arg Ser Gln Lys Lys Gln Lys Glu Arg Ile Val Val
                115                 120                 125

Asn Val Gly Ser Asn Thr Ser Ile Ile Gly Val Gly Lys Asp Ala Lys
                130                 135                 140

Ile Val Gly Gly Phe Leu Ile Lys Asn Val Asp Asn Val Ile Ile
145                 150                 155                 160

Arg Asn Ile Glu Phe Glu Ala Pro Val Asp Tyr Phe Pro Glu Trp Asp
                165                 170                 175

Pro Thr Asp Gly Thr Leu Gly Glu Trp Asn Ser Glu Tyr Asp Ser Ile
                180                 185                 190

Thr Ile Glu Gly Ser His His Ile Trp Ile Asp His Asn Thr Phe Thr
                195                 200                 205

Asp Gly Asp His Pro Asp Lys Ser Leu Gly Thr Tyr Phe Gly Arg Pro
210                 215                 220

Phe Gln Gln His Asp Gly Ala Leu Asp Ile Lys Asn Ser Ser Asp Phe
225                 230                 235                 240

Ile Thr Ile Ser Tyr Asn Val Phe Lys Asp His Asp Lys Val Thr Leu
                245                 250                 255

Ile Gly Ala Ser Asp Ser Arg Met Ala Asp Glu Gly His Leu Arg Val
                260                 265                 270

Thr Leu His His Asn Tyr Tyr Lys Asn Val Thr Gln Arg Leu Pro Arg
                275                 280                 285

Val Arg Phe Gly Gln Val His Ile Tyr Asn Asn Tyr Tyr Glu Phe Ser
290                 295                 300

Asn Leu Ala Asp Tyr Asp Phe Gln Tyr Ala Trp Gly Val Gly Val Glu
305                 310                 315                 320

Ser Lys Ile Tyr Ala Gln Asn Asn Tyr Phe Ser Phe Asp Trp Asp Ile
                325                 330                 335

Asp Pro Ser Lys Ile Ile Lys Val Trp Ser Lys Asn Glu Glu Ser Met
                340                 345                 350

Tyr Glu Ser Gly Thr Ile Val Asp Leu Pro Asn Gly Arg Arg Tyr Ile
                355                 360                 365

Asp Leu Val Ala Ser Tyr Asn Glu Ser Asn Thr Leu Gln Leu Lys Lys
                370                 375                 380

Glu Val Gly Trp Lys Pro Met Phe Tyr His Val Ile His Pro Thr Pro
385                 390                 395                 400

Ser Val Pro Ala Leu Val Lys Ala Lys Ala Gly Ala Gly Asn Leu His
                405                 410                 415

<210> SEQ ID NO 3
<211> LENGTH: 416
<212> TYPE: PRT

<213> ORGANISM: Bacillus spec.

<400> SEQUENCE: 3

```
Lys Glu Leu Gly His Asp Val Leu Lys Pro Asn Asp Gly Trp Ala Ser
1               5                   10                  15
Tyr Gly Glu Gly Thr Thr Gly Gly Ser Glu Ala Ser Pro Asp Asn Val
            20                  25                  30
Tyr Thr Val Thr Asn Lys Ser Glu Leu Val Gln Ala Leu Gly Gly Asn
        35                  40                  45
Asn His Thr Asn Gln Tyr Asn Ser Thr Pro Lys Ile Ile Tyr Val Lys
    50                  55                  60
Gly Thr Ile Glu Leu Asn Val Asp Asp Asn Asn Gln Pro Val Gly Pro
65                  70                  75                  80
Glu Tyr Tyr Asp Asp Pro His Tyr Asp Phe Glu Ala Tyr Leu Lys Glu
                85                  90                  95
Tyr Asp Pro Lys Lys Trp Gly Lys Lys Glu Val Ser Gly Pro Leu Glu
            100                 105                 110
Glu Ala Arg Ala Arg Ser Gln Lys Lys Gln Lys Glu Arg Ile Val Val
        115                 120                 125
Asn Val Gly Ser Asn Thr Ser Ile Ile Gly Val Gly Lys Asp Ala Lys
130                 135                 140
Ile Val Gly Gly Gly Phe Leu Ile Lys Asn Val Asp Asn Val Ile Ile
145                 150                 155                 160
Arg Asn Ile Glu Phe Glu Ala Pro Val Asp Phe Phe Pro Glu Trp Asp
                165                 170                 175
Pro Thr Asp Gly Glu Tyr Gly Glu Trp Asn Ser Glu Tyr Asp Ser Ile
            180                 185                 190
Thr Ile Glu Ser Ser His His Ile Trp Ile Asp His Asn Thr Phe Thr
        195                 200                 205
Asp Gly Asp His Pro Asp Lys Ser Leu Gly Thr Tyr Phe Gly Arg Pro
    210                 215                 220
Phe Gln Gln His Asp Gly Ala Leu Asp Ile Lys Asn Ser Ser Asp Phe
225                 230                 235                 240
Ile Thr Ile Ser Tyr Asn Val Phe Lys Asp His Asp Lys Val Ser Leu
                245                 250                 255
Ile Gly Ser Ser Asp Ser Arg Lys Thr Asp Glu Gly His Leu Lys Val
            260                 265                 270
Thr Leu His His Asn Tyr Tyr Lys Asn Val Thr Gln Arg Leu Pro Arg
        275                 280                 285
Val Arg Phe Gly Gln Val His Ile Tyr Asn Asn Tyr Glu Phe Ser
290                 295                 300
Asn Leu Ala Asp Tyr Asp Phe Gln Tyr Ala Trp Gly Val Gly Val Glu
305                 310                 315                 320
Ser Lys Ile Tyr Ala Gln Asn Asn Tyr Phe Ser Phe Asp Trp Asp Ile
                325                 330                 335
Asp Pro Ser Lys Ile Ile Lys Val Trp Ser Lys Asn Glu Glu Ser Met
            340                 345                 350
Tyr Glu Ser Gly Thr Ile Val Asp Leu Pro Asn Gly Arg Arg Tyr Ile
        355                 360                 365
Asp Leu Val Ala Ser Tyr Asn Glu Ser Asn Thr Leu Gln Leu Lys Lys
    370                 375                 380
Glu Val Gly Trp Lys Pro Met Phe Tyr His Val Ile His Pro Thr Pro
385                 390                 395                 400
```

-continued

Ser Val Pro Ala Leu Val Lys Ala Lys Ala Gly Ala Gly Asn Leu His
            405                 410                 415

<210> SEQ ID NO 4
<211> LENGTH: 512
<212> TYPE: PRT
<213> ORGANISM: Bacillus spec.

<400> SEQUENCE: 4

Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile
            20                  25                  30

Gln Glu Phe Lys Lys Lys Leu His Arg Asp Leu Pro Pro Thr Thr Leu
        35                  40                  45

Trp Gly Tyr Asn Ala Gln Phe Pro Gly Pro Thr Ile Glu Ala Asn Ser
    50                  55                  60

Asn Glu Pro Val Glu Val Lys Trp Ile Asn Glu Leu Pro Asn Lys His
65                  70                  75                  80

Phe Leu Pro Val Asp Trp Ser Ile Met Asn Lys Asp Leu Pro Glu Val
                85                  90                  95

Arg His Val Thr His Leu His Gly Gly Arg Thr Pro Ser Val Ser Asp
            100                 105                 110

Gly Tyr Pro Glu Ala Trp Tyr Thr Lys Asp Tyr Lys Gly Val Gly Ser
        115                 120                 125

Phe Phe Lys Glu Glu Val Tyr Arg Tyr Leu Asn Glu Gln Arg Ala Met
    130                 135                 140

Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
                165                 170                 175

Ser Leu Asn Leu Pro Glu Gly Glu Tyr Glu Val Pro Leu Ile Ile Gln
            180                 185                 190

Asp Arg Thr Phe Asn Glu Asp Gly Ser Leu Phe Tyr Pro Thr Gly Pro
        195                 200                 205

Glu Asp Gly Gly Glu Asp Leu Pro Asn Pro Ser Ile Val Pro Ala Phe
    210                 215                 220

Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Gly Ser Asn Ala
                245                 250                 255

Arg Ser Tyr Gln Leu His Leu Asp Ser Asn Gln Val Tyr Gln Ile
            260                 265                 270

Gly Ser Asp Gly Gly Leu Leu Glu Lys Pro Val Gln Met Asn Lys Ile
        275                 280                 285

Pro Ile Glu Ser Ser Glu Arg Ile Asp Val Ile Ile Asp Phe Ser Gln
    290                 295                 300

Cys Asp Gly Asp Glu Ile Val Leu Lys Asn Asp Leu Gly Pro Asp Ala
305                 310                 315                 320

Asp Ala Glu Asp Glu Thr Asn Glu Ile Met Lys Phe Lys Val Ser Lys
                325                 330                 335

Pro Leu Lys Glu Lys Asp Thr Ser Val Ile Pro Lys Arg Leu Ser Thr
            340                 345                 350

Ile Arg Ser Leu Arg Asn Asn Lys Ile Ser Thr His Arg Asn Leu Lys
        355                 360                 365

Leu Val Gly Ser Thr Asp Asp Phe Gly Arg Pro Leu Leu Leu Asn
          370                 375                 380

Asn Lys Lys Trp Ala Asp Pro Thr Thr Glu Lys Pro Lys Val Gly Asp
385                 390                 395                 400

Thr Glu Val Trp Ser Phe Ile Asn Thr Thr Asp Phe Ala His Pro Met
                405                 410                 415

His Ile His Leu Ile His Phe Gln Val Leu Asp Arg Gln Pro Phe Asp
            420                 425                 430

Leu Glu Arg Tyr Asn His Asp Gly Thr Ile Ile Tyr Thr Gly Pro Pro
            435                 440                 445

Arg Ala Pro Glu Pro Asn Glu Arg Gly Trp Lys Asp Thr Val Ser Ala
450                 455                 460

Pro Ala Gly Gln Ile Thr Arg Val Ile Gly Thr Phe Ala Pro Tyr Thr
465                 470                 475                 480

Gly Asn Tyr Val Trp His Cys His Ile Leu Glu His Glu Asp His Asp
                485                 490                 495

Met Met Arg Pro Met Lys Val Ile Asp Pro Lys Gln Arg Lys Asp Lys
                500                 505                 510

<210> SEQ ID NO 5
<211> LENGTH: 1248
<212> TYPE: DNA
<213> ORGANISM: Bacillus spec.

<400> SEQUENCE: 5

```
aaagaactgg gtcatgaagt tctgaaaccg tatgatggtt gggcagcgta tggtgaaggt      60
acaaccggtg gtgcaatggc aagtccgcag aatgtttttg ttgttaccaa tcgtaccgaa     120
ctgattcagg cactgggtgg taataatcat accaatcagt ataattccgt gccgaaaatc     180
atctatgtga aaggcaccat tgatctgaac gtggatgata taatcagcc ggttggtccg      240 gatttctata aagatccgca ttttgatttt gaggcctatc tgcgtgaata tgatccggca     300
acctggggta aaaagaagt tgaaggtccg ctggaagaag cacgcgttcg tagccagaaa      360
aaacagaaag atcgtatcat ggtttatgtg ggtagcaaca ccagcattat tggtgttggt     420
aaagacgcga aaatcaaagg tggtggtttc ctgattaaaa acgtggataa tgtgatcatc     480
cgcaacatcg aatttgaagc accgctggat tattttccgg aatgggatcc gaccgatggc     540
accctgggtg aatggaatag cgaatatgat agcattagca ttgaaggcag cagccatatt     600
tggattgatc acaataccttt accgatggc gatcatccgg atcgtagcct gggcaccctat     660 tttggtcgtc cgtttcagca gcatgatggc gcactggata tcaaaaatag cagcgatttt     720
atcaccatca gctacaacgt gtttaccaac cacgataaag ttaccctgat tggtgcaagc     780
gatagccgta tggcagatag cggtcatctg cgtgttaccc tgcatcacaa ttattacaaa     840
aatgttaccc agcgtctgcc tcgtgttcgt tttggtcagg ttcatatcta taacaactac     900 tatgagtta gcaacctggc cgattatgat tttcagtatg catggggtgt tggtgtgttt     960
agccagattt atgcacagaa caactatttc agcttcgatt gggatattga tccgagcctg    1020
attatcaaag tttggagcaa aaatgaagaa agcatgtatg aaaccggcac catcgttgat    1080
ctgccgaatg gtcgtcgtta tattgatctg gttgcaagct ataatgaaag caataccctg    1140
cagctgaaaa aagaggttac ctggaaaccg atgttctatc atgttattca tccgaccccg    1200
agcgttccgg cactggttaa agcaaaagcc ggtgcaggta atctgcat                  1248
```

<210> SEQ ID NO 6
<211> LENGTH: 1248
<212> TYPE: DNA
<213> ORGANISM: Bacillus spec.

<400> SEQUENCE: 6

```
aaagaactgg gtcatgatgt gctgaaaccg tatgatggtt gggcaagcta tggtgaaggt        60
acaaccggtg gtagcatggc aagtccgcag aatgtttata ccgttaccaa taaaaccgaa       120
ctggttcagg cactgggtgg taataatcat accaatcagt ataattccgt gccgaaaatc       180
atctatgtga aaggcaccat tgaactgaac gtggatgata ataatcagcc ggttggtccg       240
gaattctata agatccgca ttatgatttt gaagcctatc tgaaagagta tgatccgaaa        300
aaatggggca aaaagaagt tagcggtccg ctggaagaag cacgcgcacg tagccagaaa        360
aaacagaaag aacgtattgt tgtgaatgtg ggtagcaaca ccagcattat tggtgttggt       420
aaagatgcca aaattgtggg tggtggtttc ctgattaaaa acgtggataa tgtgatcatc       480
cgcaacatcg aatttgaagc accggtggat tattttccgg aatgggatcc gaccgatggc       540
accctgggtg aatggaatag cgaatatgat agcattacca ttgaaggcag ccatcatatt       600
tggatcgatc acaataccgg taccgatggc gatcatccgg ataaaagcct gggcaccat       660 tttggtcgtc cgtttcagca gcatgatggc gcactggata tcaaaaatag cagcgatttt       720
atcaccatca gctacaacgt gtttaaagac catgataaaa tgaccctgat tggtgcaagc       780
gatagccgta tggcagatga aggtcatctg cgtgttaccc tgcatcacaa ttattacaaa       840
aatgttaccc agcgtctgcc tcgtgttcgt tttggtcagg ttcatatcta taacaactac       900
tatgagttta gcaacctggc cgattatgac tttcagtatg catgggtgt tggtgttgaa       960 agcaaaatct atgcccagaa caactatttc agcttcgatt gggatattga cccgagcaaa      1020
attatcaaag tttggagcaa aaacgaagaa agcatgtatg aaagcggtac gattgttgat      1080
ctgccgaatg gtcgtcgtta tattgatctg gttgcaagct ataatgaaag caatacctg      1140 cagctgaaaa aagaggttgg ttggaaaccg atgttctatc atgttattca tccgaccccg      1200
agcgttccgg cactggttaa agcaaaagcc ggtgcaggta atctgcat                    1248
```

<210> SEQ ID NO 7
<211> LENGTH: 1248
<212> TYPE: DNA
<213> ORGANISM: Bacillus spec.

<400> SEQUENCE: 7

```
aaagaactgg gtcatgatgt gctgaaaccg aatgatggtt gggcaagcta tggtgaaggt        60
acaaccggtg gtagcgaagc aagtccggat aatgtttata ccgttaccaa taaaagcgaa       120
ctggttcagg cactgggtgg taataatcat accaatcagt ataattccac cccgaaaatc       180
atctatgtga aaggcaccat tgaactgaac gtggatgata ataatcagcc ggttggtccg       240
gaatattatg atgatccgca ttatgatttt gaagcctatc tgaaagagta tgatccgaaa       300
aaatggggca aaaagaagt tagcggtccg ctggaagaag cacgcgcacg tagccagaaa        360
aaacagaaag aacgtattgt tgtgaatgtg ggtagcaaca ccagcattat tggtgttggt       420
aaagatgcca aaattgtggg tggtggtttc ctgattaaaa acgtggataa tgtgatcatc       480
cgcaacatcg aatttgaagc accggttgat ttttttccgg aatgggatcc gaccgatggt       540
gaatatggcg aatggaatag cgaatatgat agcattacca tcgaaagcag ccatcatatt       600
tggatcgatc acaataccgg taccgatggc gatcatccgg ataaaagcct gggcaccat       660
```

| | |
|---|---|
| tttggtcgtc cgtttcagca gcatgatggc gcactggata tcaaaaatag cagcgatttt | 720 |
| atcaccatca gctacaacgt gtttaaagac catgataaag tgagcctgat tggttcaagc | 780 |
| gatagccgta aaaccgatga aggtcatctg aaagttaccc tgcatcacaa ctattacaaa | 840 |
| aatgttaccc agcgtctgcc tcgtgttcgt tttggtcagg ttcatatcta taacaactac | 900 |
| tatgagttta gcaacctggc cgattatgac tttcagtatg catggggtgt tggtgttgaa | 960 |
| agcaaaatct atgcccagaa caactatttc agcttcgatt gggatattga cccgagcaaa | 1020 |
| attatcaaag tttggagcaa aaacgaagaa agcatgtatg aaagcggtac gattgttgat | 1080 |
| ctgccgaatg tcgtcgtta tattgatctg gttgcaagct ataatgaaag caataccctg | 1140 |
| cagctgaaaa aagaggttgg ttggaaaccg atgttctatc atgttattca tccgaccccg | 1200 |
| agcgttccgg cactggttaa agcaaaagcc ggtgcaggta atctgcat | 1248 |

```
<210> SEQ ID NO 8
<211> LENGTH: 1536
<212> TYPE: DNA
<213> ORGANISM: Bacillus spec.

<400> SEQUENCE: 8
```

| | |
|---|---|
| atgcgtcgca aactggaaaa atttgttgat agcctgccga ttatggaaac cctgcagccg | 60 |
| aaaaccaaag gcaaaaacta ttatgaggtg aaaatccaag agtttaaaaa aaaactgcac | 120 |
| cgtgatctgc ctccgaccac cctgtggggt tataatgcac agtttccggg tccgaccatt | 180 |
| gaagcaaata gcaatgaacc ggttgaagtg aaatggatta tgagctgcc gaacaaacat | 240 |
| tttctgccgg ttgattggag catcatgaat aaagatctgc cggaagttcg tcatgttacc | 300 |
| catctgcatg gtggtcgtac cccgagtgtt agtgatggtt atccggaagc atggtatacg | 360 |
| aaagattata agaagtgggg cagcttcttc aaagaagagg tttatcgtta tctgaatgaa | 420 |
| cagcgtgcaa tgatgctgtg gtatcatgat cataccatgg gtattacccg tctgaataac | 480 |
| tatgcaggtc tggcaggcgc atatatcatt cgtgataaac atgaaaaaag cctgaatctg | 540 |
| cctgaaggcg aatatgaagt tccgctgatt attcaggatc gcacctttaa tgaagatggc | 600 |
| agcctgtttt atccgaccgg tccggaagat ggcggtgagg atctgccgaa tccgagcatt | 660 |
| gttccggcat ttctgggtga taccgttctg gttaatggta agtttggcc gtatctggaa | 720 |
| gttgaaccgc gtaaatatcg ttttcgtatt ctgaatggta gcaacgcccg tagctatcag | 780 |
| ctgcatctgg atagcaatca agaagtgtat cagattggtt cagatggtgg tctgctggaa | 840 |
| aaaccggtgc agatgaacaa aattccgatt gaaagcagcg aacgcattga tgtgattatc | 900 |
| gattttagcc agtgtgatgg tgatgagatt gtgctgaaaa atgatctggg tccggatgca | 960 |
| gatgccgaag atgaaaccaa tgaaatcatg aaattcaaag tgagcaaacc gctgaaagag | 1020 |
| aaagatacca gcgttattcc gaaacgtctg agcaccattc gtagcctgcg taataacaaa | 1080 |
| attagcaccc atcgtaatct gaaactggtt ggtagcaccg atgattttgg tcgtcctctg | 1140 |
| ctgctgctga caacaaaaa atgggcagat ccgaccacag aaaaaccgaa agttggcgat | 1200 |
| accgaagttt ggagctttat taacaccacc gattttgcac atccgatgca tattcatctg | 1260 |
| atccattttc aggttctgga tcgtcagccg tttgatctgg aacgttataa tcatgatggc | 1320 |
| accattatct ataccggtcc gcctcgtgca ccggaaccga tgaacgtggg ttggaaagat | 1380 |
| acagttagcg caccggcagg tcagattacc cgtgttattg gcacctttgc accgtatacc | 1440 |

```
ggtaattatg tttggcattg tcatatcctg gaacacgaag atcacgatat gatgcgtccg    1500
atgaaagtta ttgatccgaa acagcgtaaa gataaa                              1536
```

METHOD FOR PRODUCING REDUCING SUGAR FROM LIGNOCELLULOSIC SUBSTRATES

FIELD OF THE INVENTION

The invention relates to processes for the conversion of biomass into carbohydrates, notably reducing sugars. It provides means and methods for increasing the yield of enzymatic digestion of a biomass, in particular in methods wherein cellulose is converted into sugars using a cellulose-converting enzyme.

BACKGROUND OF THE INVENTION

Cellulose and lignin from plants are among the most prominent renewable carbon sources. These molecules are comprised in plants as lignocellulose structures; fibers of cellulose polymers entangled in a network of lignin polymers. Lignocellulose is composed mainly of cellulose, hemicellulose and lignin. Lignin may make up to 25% of the lignocellulosic biomass. For reducing sugar production, *Miscanthus* grass species, wood chips and the byproducts of lawn and tree maintenance are some of the more popular lignocellulosic materials. Corn stover, *Panicum virgatum* (switchgrass) and *Miscanthus* are the major biomass materials being studied today, due to their high productivity per acre. Cellulose, however, is contained in nearly every natural, free-growing plant, tree, and bush, in meadows, forests, and fields all over the world without agricultural effort or cost needed to make it grow.

The cellulose fraction of various lignocelluloses is a uniform structure consisting of β-1,4 linked glucose units. However, the biodegradability of cellulose may vary between plants, depending on the strength of association of the cellulose with other plant compounds. The composition and proportion of hemicellulose and lignin are highly dependent on the nature of the material. There is more lignin in softwoods (for example, spruce) than in hardwoods (for example, willow) or agricultural residues (for example, wheat straw or sugarcane bagasse), which makes softwood a particularly challenging material for ethanol production. The major hemicellulose component of hardwood and agricultural residues is xylan, while that of softwood is mostly mannan.

One of the most challenging tasks of this age is the conversion of cellulose into biofuels, such as ethanol. There are essentially two ways of producing ethanol from cellulose. First there are cellulolysis processes which consist of hydrolysis of sometimes pretreated lignocellulosic materials, using enzymes to break complex cellulose into simple sugars such as glucose, followed by fermentation and distillation. Second, there is also gasification that transforms the lignocellulosic raw material into gaseous carbon monoxide and hydrogen. These gases can then be converted to ethanol by fermentation or chemical catalysis.

The process involving cellulolysis can typically be divided into several stages: first, there may be a "pretreatment" phase, to make the lignocellulosic material such as wood or straw more amenable to hydrolysis. Then, the actual degradation of cellulose into reducing sugars occurs, followed by the production of ethanol from those sugars. Therein, the following steps may be distinguished, A) a hydrolysis (the actual cellulolysis) step, to break down the molecules into sugars followed by B) the separation of the sugar solution from the residual materials, notably lignin, followed by C) microbial fermentation of the sugar solution and distillation to produce roughly 95% pure ethanol.

Alternatively, sugars obtained by hydrolysis of lignocellulosic material can be subjected to further chemical or enzymatic conversions to produce vealue added chemical compounds. This if often featured as a sustainable future of industrial polymers production.

Although lignocellulose is the most abundant plant material resource, its susceptibility has been curtailed by its rigid structure. Due to the recalcitrant structure of lignocelluloses, a pretreatment step may be required prior to enzymatic hydrolysis in order to make the cellulose more accessible to enzymatic digestion.

By far, most pretreatments are done through physical or chemical means. Physical pretreatment is often called size reduction to reduce biomass physical size. Chemical pretreatment removes chemical harriers, so that the enzymes can have access to cellulose for enzymatic digestion.

To date, the available chemical pretreatment techniques include acid hydrolysis, steam explosion, ammonia fiber expansion, organosolve, sulfite pretreatment to overcome recalcitrance of lignocellulose, alkaline wet oxidation and ozone pretreatment.

In acid-catalyzed pretreatment, the major part of the hemicellulose is degraded, and the cellulose is then hydrolyzed by the use of cellulases, whereas in alkali-catalyzed pretreatment, part of the lignin is removed, and in addition to cellulases, hemicellulases are often used to hydrolyze the remaining polysaccharides.

Several bases can be used for the alkaline pretreatment of lignocellulosic material, and the effect of alkaline pretreatment depends on the lignin content of the materials. Alkaline pretreatment processes in general utilize lower temperatures and pressures than other pretreatment technologies.

Alkaline pretreatment can be carried out at ambient conditions, and pretreatment times are usually on the order of hours or days rather than minutes or seconds. Compared with acid processes, alkaline processes cause less sugar degradation, and many of the caustic salts can be recovered and/or regenerated, Sodium, potassium, calcium, and ammonium hydroxides amongst others are suitable alkaline pretreatment agents. Of these four, sodium hydroxide has been studied intensively. However, calcium hydroxide (slaked lime) has also been shown to be an effective pretreatment agent and is the least expensive per kilogram of hydroxide.

Methods for the enzymatic production of reducing sugars from lignocellulosic material are well known in the art. For example, WO 2010/000858 provides processes for hydrolyzing lignocellulose materials. It discloses the use of an enzyme mixture comprising a pectate lyase preparation derived from *Bacillus* sp, an endoxylanase composition derived from *Bacillus agaradhaerens*, a ferulic acid esterase composition, an alkaline cellulase and a mannanase in a process to hydrolyse lignocellosic material at a pH of 8.3. After 72 hours of incubation, the enzymes appeared to improve the conversion of cellulose to glucose by at most 15% whereas the maximum conversion obtained after 80 hours was about 65% of the maximum theoretical yield.

Despite of the above developments, alkaline pretreatment processes may still be improved.

SUMMARY OF THE INVENTION

We surprisingly found that a pretreatment with an alkaline pectate lyase with an amino acid sequence according to SEQ ID NO: 1, greatly improves the yield of reducing sugars in a process wherein cellulose from a lignocellulosic material is enzymatically digested into reducing sugars. Homologues of this alkaline pectate lyase enzyme appeared also to have this effect.

Hence, the invention relates to a method for producing a reducing sugar from a lignocellulosic material, wherein the lignocellulosic material is contacted in a pretreatment step (i.e. pretreated) with a pectate lyase at a pH between 9 and 12, wherein the pectate lyase comprises an amino acid sequence according to SEQ ID NO: 1 or an amino acid sequence at least 70% identical with SEQ ID NO: 1.

The invention also relates to a reducing sugar thus obtained.

The invention also relates to a composition comprising a lignocellulosic material and a pectate lyase comprising an amino acid sequence according to SEQ ID NO: 1 or an amino acid sequence that is at least 70% identical with SEQ ID NO: 1, wherein the composition has a pH between 9 and 12.

Advantageously, the pectate lyase is obtained by heterologous expression in *Escherichia coli*.

DETAILED DESCRIPTION OF THE INVENTION

Methods for the enzymatic production of reducing sugars from lignocellulosic material are well known in the art. Enzymatic digestion of lignocellulosic material is most commonly performed using cellulases and/or hemicellulases.

Cellulase is any of several enzymes produced chiefly by fungi, bacteria, and protozoans that catalyze cellulolysis, the decomposition of cellulose and of some related polysaccharides. The name is also used for any mixture or complex of various such enzymes, that act serially or synergistically to decompose cellulosic material.

Cellulases break down the cellulose molecule into monosaccharides ("simple sugars") such as beta-glucose, or shorter polysaccharides and oligosaccharides. Cellulose breakdown is of considerable economic importance, because it makes a major constituent of plants available for consumption and use in chemical reactions. The specific reaction involved is the hydrolysis of the 1,4-beta-D-glycosidic linkages in cellulose, hemicellulose, lichenin, and cereal beta-D-glucans. Because cellulose molecules bind strongly to each other, cellulolysis is relatively difficult compared to the breakdown of other polysaccharides such as starch.

Several different kinds of cellulases are known, which differ structurally and mechanistically. Synonyms, derivatives, and specific enzymes associated with the name "cellulase" include endo-1,4-beta-D-glucanase (beta-1,4-glucanase, beta-1,4-endoglucan hydrolase, endoglucanase D, 1,4-(1,3,1,4)-beta-D-glucan 4-glucanohydrolase), carboxymethyl cellulose (CMCase), avicelase, celludextrinase, cellulase A, cellulosin AP, alkali cellulase, cellulase, A 3, 9.5 cellulase, and pancellase SS. Cellulases and mixtures of different cellulases are commercially available.

Five general types of cellulases may be distinguished, based on the type of reaction catalyzed:

1) Endocellulases (EC 3.2.1.4) randomly cleave internal bonds at amorphous sites that create new chain ends.

2) Exocellulases or cellobiohydrolases (EC 3.2.1.91) cleave two to four units from the ends of the exposed chains produced by endocellulase, resulting in tetrasaccharides or disaccharides, such as cellobiose. Exocellulases are further classified into type I, that work processively from the reducing end of the cellulose chain, and type II, that work processively from the nonreducing end.

3) Cellobiases (EC 3.2.1.21) or beta-glucosidases hydrolyse the exocellulase product into individual monosaccharides.

4) Oxidative cellulases depolymerize cellulose by radical reactions, as for instance cellobiose dehydrogenase (acceptor).

5) Cellulose phosphorylases depolymerize cellulose using phosphates instead of water.

Apart from cellulases, hemicellulases may also be advantageously employed in the enzymatic production of reducing sugars from lignocellulosic material.

"Hemicellulose" is a collective term for a group of enzymes that break down hemicellulose. Xylanase and galactanase are representative enzymes that belong to the hemicellulase group.

"Hemicellulose" is a collective term for polysaccharides that can be obtained by alkaline extraction of the plant tissues and contains various lignocellulosic components of cell walls of plants (glucans, galactans, mannans, pentosans, xylans arabinoxylans, xyloglucans and glucomannans) with the exception of cellulose. They cannot be digested by human beings and are counted as roughage. In cereals, hemicelluloses are found in comparatively high proportions (2 to 12 percent) and also are referred to as fibrils.

We found that prior art methods employing one or more cellulase and/or hemicellulase for the production of reducing sugars from lignocellulosic material, such as the methods described in WO 2010/000858 may be greatly improved when the lignocellulosic material is treated or pretreated with a particular family of pectate lyases (E.C. 4.2.2.2) at a high pH. We provide herein a family of particularly suitable pectate lyases for that purpose.

In a method according to the invention, wherein a lignocellulosic material is first pretreated with a member of this particular pectate lyase family at a pH between 9 and 12, the yields of reducing sugar obtained in its subsequent enzymatic digestion with at least one cellulase or hemicellulase were greatly improved.

It was surprisingly found that polypeptides comprising an amino acid sequence according to SEQ ID NO: 1, or homologues thereof, improved the yield of reducing sugars with more than 20% as compared to the same process without the enzyme pretreatment or treatment with commercially available enzymes. Reducing sugars were obtained up to 80-85% of the theoretical yield.

A method according to the invention may be employed using only a single cellulase or hemicellulase. In a preferred embodiment, however, a plurality of different cellulases or hemicelluloses is used. Commercially available mixtures of these enzymes are particularly preferred because of their availability and ease of use.

The term "homologues" is to be interpreted as polypeptides comprising an amino acid sequence that is at least 70% identical to the amino acid sequence according to SEQ ID NO: 1. The skilled person is well aware of methods and means to make such homologues for instance by directed or random mutagenis, and screen them for activity in a standard assay, such as the one disclosed herein in example 5.

The term "high pH" as used herein indicates a strong alkalic environment, such as a pH between 9 and 12, such as between 10 and 12 or between 11 and 12. It may also refer to a pH between 9 and 10, or 9 and 11, such as between 10 and 11.

The term "pectate lyase activity" is used herein to indicate the ability of a polypeptide to cleave pectin using an eliminative cleavage of (1->4)-alpha-D-galacturonan yielding oligosaccharides with 4-deoxy-alpha-D-galact-4-enuronosyl groups at their nonreducing ends.

Pectate lyases (E.C. 4.2.2.2) favor pectate, the anion, over pectin, the methylated ester, which is the preferred substrate of pectin lyase E.C. 4.2.2.10. Pectate lyases are also known under different names, such as alpha-1,4-D-endopolygalacturonic acid lyase, endo-alpha-1,4-polygalacturonic acid lyase, endogalacturonate transeliminase, endopectin methyltranseliminase, pectate transeliminase, pectic acid lyase, pectic acid transeliminase, pectic lyase, pectin trans-eliminase, PGA lyase, polygalacturonate lyase, polygalacturonic acid lyase, polygalacturonic acid trans-eliminase, polygalacturonic transeliminase and PPase-N.

The term "at least 70%" is used herein to include at least 71%, 72%, 73%, 74%, 75%, 76%, 77%, 78%, 79%, 80%, 81%, 82%, 83%, 84%, 85%, 88%, 87%, 88%, 89%, 90% or more, such as 91%, 92%, 93%, 94%, 95%, 99%, 97%, 98%, 99%, or even 100%.

As used herein, the degree of identity between two or more amino acid sequences is equivalent to a function of the number of identical positions shared by the sequences; i.e., % identity=number of identical positions divided by the total number of aligned positions×100, excluding gaps, which need to be introduced for optimal alignment of the two sequences, and overhangs. The alignment of two sequences is to be performed over the full length of the polypeptides.

The comparison (aligning) of sequences is a routine task for the skilled person and can be accomplished using standard methods known in the art. For example, a freeware conventionally used for this purpose is "Align" tool at NCBI recourse http://blast.ncbi.nlm.nih.gov/Blast.cgi?PAGE_TYPE=BlastSearch&BLAST_SPEC=blast2seq&LINK_LOC=align2seq, Other commercial and open software such as Vector NTI are also suitable for this purpose.

The term "lignocellulosic material" refers to a material that comprises (1) cellulose, hemicellulose, or a combination thereof, and (2) lignin. The term also encompasses such material that has been pretreated in order to decrease the integrity of the material thereby making the lignocellulosic material more accessible to enzymatic digestion with cellulases and/or hemicellulases. Such pretreatment may include mechanical pretreatment, chemical pretreatment of enzymatic pretreatment.

Examples of a lignocellulosic material that may advantageously be used in the methods of the invention include materials comprising corn stover, bioenergy crops, agricultural residues, municipal solid waste, industrial solid waste, yard waste, wood and forestry waste, sugar cane, switchgrass, wheat straw, hay, barley, barley straw, rice straw, grasses, waste paper, sludge or byproducts from paper manufacture, corn grain, corn cobs, corn husks, grasses, wheat, wheat straw, hay, rice straw, sugar cane bagasse, sorghum, soy, trees, branches, wood chips, sawdust and any combination thereof.

The term "reducing sugar" is used herein to refer to any sugar that is capable of acting as a reducing agent because it has a free aldehyde group or a free ketone group. All monosaccharides are reducing sugars, along with some disaccharides, oligosaccharides, and polysaccharides. The common dietary monosaccharides galactose, glucose and fructose are all reducing sugars. The amount of reducing sugars may conveniently be measured by a number of methods available in the art and known to the skilled person. Reducing sugar levels as referred herein were determined by the Dinitrosalicylic Acid Method (DNS method, Sadasivam S., Manickam A., "Carbohydrates" in Biochemical methods, New Age Internatioal Ltd Publishers, 2nd edition, 2005, p. 6).

As detailed in the examples section, we incubated corn stover with enzyme solutions comprising a pectate lyase according to SEQ ID NO: 1 or its homologues according to SEQ ID NO: 2 or SEQ ID NO: 3 (93% and 89% identical to SEQ ID NO: 1 respectively). After an alkaline pretreatment at pH 10 for 120 minutes at 65 degrees Celsius, the corn stover was digested with a commercially available cellulase cocktail for biofuel applications for 72 hours at 60 degrees Celsius. We observed that the yield in reducing sugars improved from 430 mg reducing sugar per gram of corn stover to up to 550 mg, an improvement of 28%. Similar increases were observed when the corn stover was pretreated with the homologous enzymes according to SEQ ID NO: 2 or SEQ ID NO: 3 (table 1). Alkaline pretreatments were also performed at pH 9 and pH 12. Also in these cases, a remarkable improvement in the yield of reducing sugars was observed.

Hence, in one embodiment, the invention relates to a method for producing a reducing sugar from a lignocellulosic material employing at least one cellulase or hemicellulase, wherein the lignocellulosic material is pretreated (i.e. contacted in a pretreatment step) with a pectate lyase at a pH between 9 and 12, wherein the pectate lyase comprises an amino acid sequence according to SEQ ID NO: 1 or an amino acid sequence at least 70% identical with SEQ ID NO: 1.

Pre-treatment is carried out before or during hydrolysis with cellulases or hemicellualses. The goal of pre-treatment is to reduce the particle size, separate and/or release cellulose; hemicellulose and/or lignin and in this way increase the rate of hydrolysis.

The lignocellulose-containing material may according to the invention be biologically pre-treated before or during hydrolysis in accordance with the methods as described herein.

Preferably, the enzymatic pre-treatment is carried out prior to the hydrolysis. Alternatively, enzymatic pre-treatment may be carried out simultaneously with hydrolysis, such as simultaneously with addition of one or more cellulases or hemicellulases.

The term "enzymatic pre-treatment" refers to any pre-treatment employing an enzyme which promotes the separation and/or release of cellulose, hemicellulose, and/or lignin from the lignocellulose-containing material. Known biological pre-treatment techniques involve applying lignin-solubilizing microorganisms (see, for example, Hsu, T.-A., 1996, Pretreatment of biomass, in Handbook on Bioethanol: Production and Utilization, Wyman, C. E., ed., Taylor & Francis, Washington, D.C., 179-212; Ghosh, P., and Singh, A., 1993, Physicochemical and biological treatments for enzymatic/microbial conversion of lignocellulosic biomass, Adv. Appl. Microbiol, 39: 295-333; McMillan, J. D., 1994, Pretreating lignocellulosic biomass: a review, in Enzymatic Conversion of Biomass for Fuels Production, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in Advances in Biochemical Engineering/Biotechnology, Scheper, T., ed., Springer-Verlag Berlin Heidelberg, Germany, 65: 207-241; Olsson, L., and Hahn-Hagerdal, B., 1996, Fermentation of lignocellulosic hydrolysates for ethanol production, Enz. Microb. Tech. 18: 312-331; and Vallander, L., and Eriksson, K.-E. L., 1990, Production of ethanol from lignocellulosic materials: State of the art, Adv. Biochem. Eng./Biotechnol, 42: 63-95).

The pre-treated lignocellulose-containing material is hydrolyzed enzymatically to break down especially hemicellulose and/or cellulose into fermentable sugars. According to the invention the enzymatic hydrolysis may also be performed in several steps.

Some, if not most reducing sugars may be used as a substrate for fermenting micro-organisms. Such sugars are often referred to as fermentable sugars. The production of fermentable sugars is preferred because micro-organisms are preferred for the further synthesis of useful molecules from the sugars obtained in the methods as described herein, Hence, the invention also relates to a method as described above, wherein the reducing sugar is a fermentable sugar.

In another preferred embodiment, the method may also be employed to increase the yield of reducing sugars obtained from a material comprising lignocellulose with a high content of lignin, such as wood, Hence, the methods according to the invention could be further improved if the pretreatment was conducted in the simultaneous presence of a lignin-degrading enzyme, such as a laccase, more preferably, an alkaline Cot A laccase. This was found to be particularly advantageous when employing high-lignin containing lignocellulosic material Furthermore, in spite of the fact that grassy biomass is considered to have a low lignin content, we surprisingly found that the method employing grassy materials as described above could also be further improved, if the pretreatment was conducted in the simultaneous presence of a lignin-degrading enzyme, such as a laccase, more preferably, an alkaline Cot A laccase. Hence, in one embodiment, the invention relates to a method as described above, wherein the lignocellulosic material is contacted with an enzyme capable of degrading lignin, such as a laccase, more in particular an alkaline laccase, even more in particular a CotA laccase, such as an alkaline Cot A laccase, simultaneously with the pectate lyase.

The term "alkaline laccase" refers to an enzyme with laccase activity that is active at alkaline conditions.

Laccases (EC 1.10.3.2) are enzymes having a wide taxonomic distribution and belonging to the group of multicopper oxidases. Laccases are eco-friendly catalysts, which use molecular oxygen from air to oxidize various phenolic and non-phenolic lignin-related compounds as well as highly recalcitrant environmental pollutants, and produce water as the only side-product. These natural "green" catalysts are used for diverse industrial applications including the detoxification of industrial effluents, mostly from the paper and pulp, textile and petrochemical industries, use as bioremediation agent to clean up herbicides, pesticides and certain explosives in soil. Laccases are also used as cleaning agents for certain water purification systems. In addition, their capacity to remove xenobiotic substances and produce polymeric products makes them a useful tool for bioremediation purposes.

Laccases were originally discovered in fungi, they are particularly well studied in White-rot fungi and Brown-rot fungi. Later on, laccases were also found in plants and bacteria. Laccases have broad substrate specificity; though different laccases can have somewhat different substrate preferences. Main characteristic of laccase enzyme is its redox potential, and according to this parameter all laccases can be divided in three groups (see, for example, Morozova, O. V., Shumakovich, G. P., Gorbacheva, M. a., Shleev, S. V., & Yaropolov, a. I. (2007). "Blue" laccases. Biochemistry (Moscow), 72(10), 1136-1150. doi:10.1134/ 50006297907100112): high redox potential laccases (0.7-0.8 V), medium redox potential laccases (0.4-0.7 V) and low redox potential laccases (<0.4V). It is believed that low redox potential limits the scope of substrates which the enzyme can possibly oxidize, and vice versa. All high redox potential laccases and the upper part of the medium redox potential laccases are fungal laccases. Industrial application of laccases is mostly if not entirely relying on fungal laccases.

CotA is a bacterial laccase and is a component of the outer coat layers of *bacillus* endospore. It is a 65-kDa protein encoded by the cotA gene (Martins, O., Soares, M., Pereira, M. M., Teixeira, M., Costa, T., Jones, G. H., & Henriques, A. O. (2002). Molecular and Biochemical Characterization of a Highly Stable Bacterial Laccase That Occurs as a Structural Component of the *Bacillus subtilis* Endospore Coat. Biochemistry, 277(21), 18849-18859. doi:10.1074/jbc.M200827200). CotA belongs to a diverse group of multi-copper "blue" oxidases that includes the laccases. This protein demonstrates high thermostability, and resistance to various hazardous elements in accordance with the survival abilities of the endospore. The redox-potential of this protein has been reported to be around 0.5 mV, which places it in the range of medium-redox-potential laccases.

As detailed in the examples section, we incubated corn stover with an enzyme solution comprising a pectate lyase according to SEQ ID NO: 1 together with a laccase according to SEQ ID NO: 4. After an alkaline pretreatment at pH 10 for 120 minutes at 65 degrees Celsius, the corn stover was digested with a commercially available cellulase cocktail for biofuel applications for 72 hours at 60 degrees Celsius. We observed that this simultaneous pretreatment resulted in a yield of 585 mg of reducing sugar per gram feedstock, an improvement of 36% when compared to the control preincubation without the enzymes, and an improvement of 6% over the pretreatment with the pectate lyase according to SEQ ID NO: 1 alone. Most remarkably, the yield of the method wherein the lignocellulosic material was pretreated with a pectate lyase and a laccase under alkaline conditions, closely approached the maximum theoretical yield of 650 mg reducing sugar per gram feedstock (table 1).

In a preferred embodiment, the alkaline COT A laccase is a polypeptide comprising an amino acid sequence according to SEQ ID NO: 4 or an amino acid sequence at least 90% identical with SEQ ID NO: 4.

The term "at least 90%" is used herein to include at least 91%, 92%, 93%, 94%, 95%, 99%, 97%, 98%, 99%, or even 100%.

After preincubation, reducing sugars are preferably obtained from the pretreated material by enzymatic digestion of cellulose. Without wanting to be bound by theory, the inventors believe that the pretreatment steps as described herein make the cellulose more accessible to enzymatic digestion. Hence, the invention also relates to a method for making cellulose in a biomaterial more accessible to enzymatic digestion, such as cellulose-degrading enzymes.

Cellulose-degrading enzymes are known in the art and commercially available. They are usually offered in combination preparations, for example, CELLIC CTEC3™ or CTEC2™ preparations (from Novozymes, Denmark) which are compositions of enzymes comprising cellulases, [beta]-glucosidases and hemi-cellulase; or CELLIC HTEC3™ or HTEC2™ (also from Novozymes, Denmark) which is a composition of enzymes comprising endoxylanase and cellulase.

In summary, the invention relates to a method as described herein, wherein lignocellulosic material is contacted with an enzyme capable of degrading cellulose after being pretreated with an alkaline pectate lyase.

Since most cellulose-degrading enzymes are active at neutral or acidic pH, the pH of the composition comprising the lignocellulosic material may be lowered to a suitable range after pretreatment. The skilled person is well aware of the means to accomplish that. The temperature may also be adjusted to an optimal temperature for enzymatic digestion using at least one cellulase and/or hemicellulase. This will entirely depend on the choice of the enzymes for this purpose, such is again well-known to the skilled person.

Advantageously, the cellulose-degrading enzyme is selected from the group consisting of cellulase; hemi-cellulase; [beta] 1-4 endoglucanases (E.C. [beta] 1-4 exoglucanases (E.C. 3.2.1.9.1), [beta]-glucosidases (E.C. 3.2.1.2.1), and endoxylanases.

In a further preferred method according to the invention, the lignocellulose material may advantageously be pretreated before the enzyme or enzymes are added.

The term "pretreated" as used herein may therefore also refer to a treatment that occurs before the enzymatic treatment, either pectate lyases, laccases or cellulose-degrading enzymes or combinations thereof. Pretreatment may also consist of a steam treatment, such as a dilute acid steam treatment or a steam explosion treatment is applied to the biomass or lignocellulose material. One of the goals of the steam treatment is to depolymerize the lignin in the biomass to a sufficient extent to allow an enzyme or mixture of enzymes to convert the cellulose and hemi-cellulose in the biomass into less complex sugars in a subsequent step.

The method as described herein may even be further improved when the lignocellulosic material is pretreated before the enzyme or enzymes are added. Preferably, such a pretreatement is a mechanical pretreatment. Hence, in one embodiment, the invention relates to a method as described herein wherein the lignocellulosic material is pretreated before the material is contacted with the pectate lyase, an enzyme capable of degrading cellulose (such as cellulase or hemicellulase, or an enzyme capable of degrading lignin, such as a laccase. Particularly preferred in this sense is a pretreatment by a steam explosion step or ammonia fiber explosion step.

In a further preferred embodiment, the invention relates to a method as described herein wherein the pectate lyase has an amino acid sequence that is at least 89% identical to the sequence according to SEQ ID NO:1, preferably at least 93%, such as at least 96%, 97%, 98% or 99%.

In another embodiment, the invention relates to a composition comprising a lignocellulosic material and a pectate lyase comprising an amino acid sequence according to SEQ ID NO: 1 or an amino acid sequence that is at least 70% identical with SEQ ID NO: 1, wherein the composition has a pH between 9 and 12.

The lignocellulosic material of such a composition is then advantageously selected from the group consisting of corn stover, bioenergy crops, agricultural residues, municipal solid waste, industrial solid waste, yard waste, wood and forestry waste, sugar cane, switchgrass, wheat straw, hay, barley, barley straw, rice straw, grasses, waste paper, sludge or byproducts from paper manufacture, corn grain, corn cobs, corn husks, grasses, wheat, wheat straw, hay, rice straw, sugar cane bagasse, sorghum, soy, trees, branches, wood chips and sawdust.

Such compositions may additionally comprise an enzyme capable of degrading cellulose or an alkaline enzyme capable of degrading lignin. The enzyme capable of degrading cellulose is then preferably selected from the group consisting of cellulases and hemi-cellulases. This group encompasses [beta] 1-4 endoglucanases (E.G. 3.2.1.4), [beta] 1-4 exoglucanases (E.G. 3.2.1.9.1), [beta]-glucosidases (E.G. 3.2.1.2.1) and endoxylanases.

The enzyme capable of degrading lignin may then advantageously comprise a laccase, such as an alkaline laccase or a CotA laccase or an alkaline CotA laccase comprising an amino acid sequence according to SEQ ID NO: 4 or an amino acid sequence at least 90% identical with SEQ ID NO: 4. The pectate lyase in such a composition may advantageously comprise an amino acid sequence that is at least 89% identical to the sequence according to SEQ ID NO: 1, preferably 93%, such as 96%, 97%, 98% or 99%.

It is also particularly preferred when the method according to the invention is performed with a pectate lyase obtained by heterologous expression in *Escherichia coli*.

In certain processes, the temperature of the biomass or lignocellulosic material to be treated may be in excess of the enzyme inactivation temperature. Since a high temperature may inactivate enzymes by denaturing its amino acid chain, the enzyme may advantageously be added to the biomass at a point below the enzyme inactivation temperature. The enzymes may be added within the functional temperature range(s) or at the optimal temperature(s) of the enzyme. To save energy, the enzymes may be added after the biomass has cooled below the inactivation temperature and that the enzymatic process is completed sufficiently before the temperature has dropped below the optimal functional temperature of the enzyme. Naturally, it is also an option to maintain a desired temperature by cooling or heating the biomass or lignocellulosic material. Adding a dilution liquid, such as water at a certain temperature, may be used to cool the biomass.

In one embodiment, the enzyme pretreatment process may be performed at a specific temperature such as, for example at from 30 degrees C. to 70 degrees C.; 40 degrees C. to 65 degrees C.; or 45 degrees C. to 60 degrees C., or at room temperature or lower. More thermostable enzymes may be used when the temperature requirements are higher. Thermostable laccases, cellulases and pectate lyases are well known in the art.

The contacting of the lignocellulosic material with an enzyme can be performed for a period of time up to one day. While longer enzymatic digestions are possible, such as two, three or four days, a shorter period of time such as 60 minutes, 2 hours, 10 hours, 20 hours, 30 hours, 40 hours, 60 hours or 72 hours or any time less than these values or any time between any of two of these values may be used for practical or economic reasons. In another preferred embodiment, the enzymatic digestions can take 50, 100, 150 or 200 hours or any time less than these values or any time between any of two of these values. In one embodiment, a preferred period of pretreatment is for about 2 hours.

EXAMPLES

Example 1: Preparation of a Polypeptide According to SEQ ID NO: 1

The DNA construct disclosed in Takao et al., Biosci. Biotechnol. Biochem. (2001) 65: 322-329 encoding the polypeptide according to SEQ ID NO: 1 was optimized for expression in *E. coli* and commercially synthesized and cloned into a standard plasmid vector pET28a+ under the control of T7-RNA-polymerase promoter for expression in

*Escherichia coli* BL21(DE3). The nucleotide sequence of the construct is provided herein as SEQ ID NO: 7

Example 2: Preparation of Variants of a Polypeptide According to SEQ ID NO: 1 with Pectate Lyase Activity Homologous protein sequences (according to SEQ ID NO: 2 and SEQ ID NO: 3) were generated by random mutagenesis of SEQ ID NO:s 7 and SEQ ID NO: 8 using error-prone PCR essentially as described (Curr Protoc Mol Biol. 2001 May; Chapter 8: Unit 8.3, doi: 10.1002/0471142727.mb0803s51, Random mutagenesis by PCR. Wilson DS1, Keefe A D) using a commercial random PCR mutagenesis kit (QuikChange® II XL Site-Directed Mutagenesis kit by Agilent Technologies). More in particular, the DNA sequence of SEQ ID NO: 8 was obtained from SEQ ID NO: 7 encoding the polypeptide according to SEQ ID NO: 1. The DNA sequence of SEQ ID NO: 9 was obtained by random mutagenesis of SEQ ID NO: 8 encoding the polypeptide, according to SEQ ID NO: 2. SEQ ID NO: 9 is the DNA sequence encoding the polypeptide according to SEQ ID NO: 3.

PCR fragments resulting from error-prone PCR were cloned to the plasmid vector pET28a+ under the control of T7-RNA-polymerase promoter for expression in *Escherichia coli* BL21(DE3), and screened for pectate lyase activity of the recombinant proteins.

Active clones were subjected to further rounds of randomization using the same protocol. The polypeptide according to SEQ ID NO: 2 exhibited pectate lyase activity and was found to be 93% identical with SEQ ID NO: 1, The polypeptide according to SEQ ID NO: 3 also exhibited pectate lyase activity and was found to be 89% identical with SEQ ID NO: 1.

Example 3: Heterologous Expression of Polypeptides with Pectate Lyase Activity For recombinant expression in *E. coli*, recombinant genes were cloned into pET-28 commercial expression vector under the control of T7 bacteriophage promoter.

Protein production was carried out in *E. coli* BL21(DE3) strain according to the plasmid manufacturer protocol available at http://richsingiser.com/4402/Novagen %20pET %20system%20manual.pdf. The incubation temperature for protein production was 30 degrees C., which was found optimal for maximum yield of the active protein. Cells were lysed using lysis buffer (20 mM Sodium Citrate pH7.4, 1% Triton X100, 0.5 mM CaCl) and heated at 60 degrees C. for 20 minutes. Coagulated cell debris was removed by centrifugation. The thermostable recombinant pectate lyases were detected in the soluble fraction only, consistent with the notion that they were thermostable enzymes.

Example 4 Heterologous Expression of Polypeptides with Laccase Activity

For recombinant expression in *E. coli*, recombinant genes were cloned into pET-28 commercial expression vector under the control of T7 bacteriophage promoter.

Protein production was carried out in *E. coli* BL21(DE3) strain according to the plasmid manufacturer protocol available at http://richsingiser.com/4402/Novagen %20pET %20system%20manual.pdf. The incubation temperature for protein production was 30 degrees C., which was found optimal for maximum yield of the active protein. Cells were lysed using laccase lysis buffer (Sodium Citrate pH 7.4, 1% Triton X100, 1 mM CuCl2) and heated at 70 degrees C. for 20 min. Coagulated cell debris was removed by centrifugation. The thermostable recombinant laccases were detected in the soluble fraction only, consistent with the notion that they are thermostable enzymes.

Example 5: Pectate Lyase Activity Assay

Pectate lyase activity assay was carried out essentially as described in Takao M, Nakaniwa T, Yoshikawa K, Terashita T, Sakai T., "Purification and characterization of thermostable pectate lyase with protopectinase activity from thermophilic *Bacillus* sp. TS 47". Biosci Biotechnol Biochem. 2000 64:2360-7. In more detail, pectate lyase activity was assayed by measuring the increase in absorbance at 235 nm of the reaction mixture, Polygalacturonic acid (PGA) sodium salt from de-methylated citrus pectin (purchased from MegaZyme) was used as substrate. A reaction mixture containing 1 ml of 0.1% PGA in 10 mM Tris-HCl buffer, pH 8.0 and 0.5 mM CaCl2), and an appropriate amount of enzyme solution was incubated for 30 minutes at 60 degrees C.

The reaction was stopped by placing the mixture in 100 degrees C. (boiling water bath) for 5 min. Pectate lyase activity was calculated from the difference in absorption of the reaction mixture at 235 nm at the start and at the end of the reaction.

One unit of pectate lyase activity was defined as the enzyme amount oxidizing 1 micro mole of substrate per minute. Using absorption coefficient of the unsaturated bond at the 4-5 position of the uronic acid residue at 235 nm 4 600 mol-1×cm-1.

Example 6: Laccase Activity Measurement

The term "laccase activity" is used herein to mean the capability to act as a laccase enzyme, which may be expressed as the maximal initial rate of the specific oxidation reaction. Relative activity was measured by oxidation of syringaldazine. Reaction course was monitored by change in absorbance at 526 nM (extinction coefficient of syringaldazine at 526 nm is 65 000 M-1 cm-1). The appropriate reaction time was determined to provide initial rates of oxidation when color development is linear in time. Syringaldazine concentration in the reaction mixture was 1 mM to provide maximum initial rates (substrate saturation conditions).

Typically, reactions were carried out in 1 ml volume of 50 mM Tris-HCl buffer pH 8, the substrate was preheated to the desired temperature (60 degrees Celsius) and reaction was initiated by the addition of the enzyme. After the reaction time has elapsed, absorbance at 526 nm of the reaction mixtures was determined by a spectrophotometer, and the absorbence of the blank sample (containing no enzyme) was subtracted.

One unit of laccase activity was defined as the enzyme amount oxidising 1 micro mole of substrate per minute.

Example 7: Effect of Enzymatic Pretreatment on Reducing Sugar Yield

Reducing sugars were produced from corn stover using a conventional process wherein the corn stover was mechanically pretreated by reducing the particle size, followed by an enzymatic pretreatment at alkaline conditions.

Mechanical pretreatment involved reducing the particle size of corn stover in a Thomas knife mill (Arthur H. Thomas Company, Philadelphia, Pa., USA) followed by screening in a Tyler portable sieve shaker, model KX-24 (Combustion Engineering, Mentor, Ohio, USA). The particle size ranged from 8- to 200-mesh.

Alkaline pretreatment was carried out in a 1 liter reactor wherein the temperature was controlled by water circulation through the jacket and thorough mixing was provided by propeller blades.

The reactor was loaded with 55 gram (dry weight) of corn stover, and 450 ml of 0.5% NaOH was added. The pH of this suspension was found to be between 10 and 11.

After the biomass was well mixed and equilibrated to 65 degrees Celsius, enzyme solution (10 ml of enzyme in lysis buffer) or the same volume of lysis buffer without the enzyme (control) was added and the reaction was allowed to continue for 120 minutes at 65 degrees Celsius.

The pectate lyases disclosed herein were dosed at 10,000,000 units of pectate lyase (standard activity measured at pH 8.0, see example 5), per ton of dry corn stover material.

Commercial preparation Pectinex® was obtained from Novozymes, Denmark, and used at the same dosage according to specific activity as indicated by the manufacturer.

The lignin degrading enzyme according to SEQ ID NO: 4 was used at 10 millikatal/ton of dry corn stover. One katal is defined as the amount of enzyme needed to convert 1 mole of substrate in 1 sec. A unit is defined as the amount of enzyme needed to convert 1 micromole of substrate in 1 minute, hence 10 millikatal equals 600,000 units.

After pretreatment, the reactors were immediately cooled by passing ice-cold water through the jackets. Corn stover from two duplicate reactions treated under the same conditions was recovered, combined, and washed intensively with deionized water.

The biomass was then suspended in 100 mM succinic acid at pH 5.0, to make up a suspension of 50 grams of dry weight of biomass per kilogram of suspension.

Enzymatic hydrolysis of the pretreated biomass was carried out at 60 degrees Celsius for 72 hours using Alternafuel® CMAX™ from Diadic International Inc (USA) a commercially available cellulase cocktail for biofuel applications. Dosing was performed according to the manufacturer's instructions.

After the hydrolysis, reducing sugar levels were determined by the Dinitrosalicylic Acid Method (DNS method, Sadasivam S., Manickam A., "Carbohydrates" in Biochemical methods, New Age Internatioal Ltd Publishers, 2nd edition, 2005, p. 6). The results are shown in Table 1.

We observed a large increase in yield when the lignocellulosic material was pretreated under alkaline conditions with a pectate lyase according to SEQ ID NO: 1, SEQ ID NO: 2 or SEQ ID NO: 3, as compared to the same pretreatment without the enzymes.

The yield in reducing sugars was even further improved when the biomass was simultaneously treated with a lignin-degrading enzyme according to SEQ ID No: 4. Notably, pretreatment with the commercial pectinase Pectinex® from Novozymes had no effect on reducing sugar yield (table 1).

Other lignocellulosic materials such as sugar cane, switchgrass, wheat straw and soft wood were also tested with the enzymes as disclosed herein, with equivalent results. The pH of the pretreatment compositions varied from pH 9 to pH 12.

In all cases a clear advantage of the pretreatment with the pectate lyase enzymes was observed.

TABLE 1

Effect of enzyme pretreatment on reducing sugar yield from lignocellulosic biomass.

| Corn stover pretreatment | Cellulase [mg sugar/ gram feedstock] | Improvement of yield [%] | Theoretical yield [mg sugar/ gram feedstock] | Percentage of theoretical yield [%] |
|---|---|---|---|---|
| Reference | 430 | 0% | 650 | 66% |
| SEQ ID NO: 1 | 550 | 28% | 650 | 85% |
| SEQ ID NO: 2 | 520 | 21% | 650 | 80% |
| SEQ ID NO: 3 | 530 | 23% | 650 | 82% |
| SEQ ID NO: 1 + SEQ ID NO: 4 | 585 | 36% | 650 | 90% |
| Pectinex ® | 420 | −2% | 650 | 65% |

Example 8: Sequences Provided Herein

Amino acid sequence and nucleotide sequences are separately provided herewith according to the WIPO ST25 standard. For convenience, the sequences are also reproduced herein in table 2.

SEQ ID NO: 1 is derived from the prior art and has been disclosed in Takao et al, Biosci. Biotechnol. Biochem. (2000) 64: 2360-2367 and in Takao et al., Biosci. Biotechnol. Biochem. (2001) 65: 322-329.

SEQ ID NO: 2 was obtained by random mutagenesis of the DNA encoding SEQ ID NO: 1 (shown herein as SEQ ID NO: 5) as described in example 2.

SEQ ID NO: 3 was obtained by random mutagenesis of the DNA encoding SEQ ID NO: 2 (shown herein as SEQ ID NO: 6). The DNA encoding the polypeptide according to SEQ ID NO: 3 is shown herein as SEQ ID NO: 7. The amino acids deviating from the wild type sequence of SEQ ID NO: 1 are shown in capital letters.

The polypeptide with an amino acid sequence according to SEQ ID NO: 2 is a homologue of the polypeptide according to SEQ ID NO: 1, These two polypeptides have 385 of the 416 amino acids in common, in other words they are 93% identical.

The polypeptide according to SEQ ID NO: 3 is also a homologue of the polypeptide according to SEQ ID NO: 1, These two polypeptides have 369 of the 416 amino acids in common, in other words they are 89% identical.

SEQ ID NO: 4 and SEQ ID NO: 8 are the protein and DNA sequence respectively from a thermostable and alkaline Cot A laccase.

TABLE 2

Amino acid and nucleotide sequences provided herein

| SEQ ID NO: | Sequence | | | | |
|---|---|---|---|---|---|
| 1 | 1 | kelghevlkp | ydgwaaygeg | ttggamaspq | nvfvvtnrte | liqalggnnh tnqynsvpki |
| | 61 | iyvkgtidln | vddnnqpvgp | dfykdphfdf | eaylreydpa | twgkkevegp leearvrsqk |
| | 121 | kqkdrimvyv | gsntsiigvg | kdakikgggf | liknvdnvii | rniefeapld yfpewdptdg |

TABLE 2-continued

Amino acid and nucleotide sequences provided herein

| SEQ ID NO: | Sequence |
|---|---|
| | 181 tlgewnseyd sisiegsshi widhnftftdg dhpdrslgty fgrpfqqhdg aldiknssdf<br>241 itisynvftn hdkvtligas dsrmadsghl rvtlhhnyyk nvtqrlprvr fgqvhiynny<br>301 yefsnladyd fqyawgvgvf sqiyaqnnyf sfdwdidpsl iikvwsknee smyetgtivd<br>361 lpngrryidl vasynesntl qlkkevtwkp mfyhvihptp svpalvkaka gagnlh |
| 2 | 1 kelghDvlkp ydgwaSygeg ttggSmaspq nvYTvtnKte lVqalggnnh tnqynsvpki<br>61 iyvkgtiEln vddnnqpvgp EfykdphYdf eaylKeydpK KwgkkevSgp leeearArsqk<br>121 kqkEriVvNv gsntsiigvg kdakiVgggf liknvdnvii rniefeapVd yfpewdptdg<br>181 tlgewnseyd siTiegsHhi widhnftftdg dhpdKslgty fgrpfqqhdg aldiknssdf<br>241 itisynvfKD hdkvtligas dsrmadEghl rvtlhhnyyk nvtqrlprvr fgqvhiynny<br>301 yefsnladyd fqyawgvgvE sKiyaqnnyf sfdwdidpsK iikvwsknee smyeSgtivd<br>361 lpngrryidl vasynesntl qlkkevGwkp mfyhvihptp svpalvkaka gagnlh |
| 3 | 1 kelghDvlkp NdgwaSygeg ttggSEaspD nvYTvtnKSe lVqalggnnh tnqynsTpki<br>61 iyvkgtiEln vddnnqpvgp EYyDdphYdf eaylKeydpK KwgkkevSgp leeearArsqk<br>121 kqkEriVvNv gsntsiigvg kdakiVgggf liknvdnvii rniefeapVd Ffpewdptdg<br>181 EYgewnseyd siTiesSshhi widhnftftdg dhpdKslgty fgrpfqqhdg aldiknssdf<br>241 itisynvfKD hdkvSligSs dsrKTdEghl Kvtlhhnyyk nvtqrlprvr fgqvhiynny<br>301 yefsnladyd fqyawgvgvE sKiyaqnnyf sfdwdidpsK iikvwsknee smyeSgtivd<br>361 lpngrryidl vasynesntl qlkkevGwkp mfyhvihptp svpalvkaka gagnlh |
| 4 | 1 mrrklekfvd slpimetlqp ktkgknyyev kiqefkkklh rdlppttlwg ynaqfpgpti<br>61 eansnepvev kwinelpnkh flpvdwsimn kdlpevrhvt hlhggrtpsv sdgypeawyt<br>121 kdykevgsff keevyrylne qrammlwyhd htmgitrlnn yaglagayii rdkhekslnl<br>181 pegeyevpli iqdrtfnedg slfyptgped ggedlpnpsi vpaflgdtvl vngkvwpyle<br>241 veprkyrfri lngsnarsyq lhldsnqevy qigsdgglle kpvqmnkipi esseridvii<br>301 dfsqcdgdei vlkndlgpda daedetneim kfkvskplke kdtsvipkrl stirslrnnk<br>361 isthrnlklv gstddfgrpl lllnnkkwad pttekpkvgd tevwsfintt dfahpmhihl<br>421 ihfqvldrqp fdleryrnhdg tiiytgppra pepnergwkd tvsapagqit rvigtfapyt<br>481 gnyvwhchil ehedhdmmrp mkvidpkqrk dks |
| 5 | aaagaactgg gtcatgaagt tctgaaaccg tatgatggtt gggcagcgta tggtgaaggt    60<br>acaaccggtg gtgcaatggc aagtccgcag aatgttttg ttgttaccaa tcgtaccgaa    120<br>ctgattcagg cactgggtgg taataatcat accaatcagt ataattccgt gccgaaaatc    180<br>atctatgtga aaggcaccat tgatctgaac gtggatgata taatcagcc ggttggtccg    240<br>gatttctata aagatccgca ttttgatttt gaggcctatc tgcgtgaata tgatccggca    300<br>acctgggtga aaaaagaagt tgaaggtccg ctggaagaag cacgcgttcg tagccagaaa    360<br>aaacagaaag atcgtatcat ggtttatgtg ggtagcaaca ccagcattat tggtgttggt    420<br>aaagacgcga aaatcaaagg tggtggtttc ctgattaaaa acgtggataa tgtgatcatc    480<br>cgcaacatcg aatttgaagc accgctggat tattttccgg aatgggatcc gaccgatggc    540<br>accctgggtg aatggaatag cgaatatgat agcattagca ttgaaggcag cagccatatt    600<br>tggattgatc acaataccct taccgatggc gatcatccgg atcgtagcct gggcacctat    660<br>tttggtcgtc cgtttcagca gcatgatggc gcactggata tcaaaaatag cagcgatttt    720<br>atcaccatca gctacaacgt gtttaccaac cacgataaag ttaccctgat tggtgcaagc    780<br>gatagccgta tggcagatag cggtcatctg cgtgttaccc tgcatcacaa ttattacaaa    840<br>aatgttaccc agcgtctgcc tcgtgttcgt tttggtcagg ttcatatcta taacaactac    900<br>tatgagttta gcaacctggc cgattatgat tttcagtatg catggggtgt tggtgtgttt    960<br>agccagattt atgcacagaa caactatttc agcttcgatt gggatattga tccgagcctg   1020<br>attatcaaag tttggagcaa aaatgaagaa agcatgtatg aaaccggcac catcgttgat   1080<br>ctgccgaatg gtcgtcgtta tattgatctg gttgcaagct ataatgaaag caatacctg    1140<br>cagctgaaaa agaggttac ctggaaaccg atgttctatc atgttattca tccgaccccg    1200<br>agcgttccgg cactggttaa agcaaaagcc ggtgcaggta atctgcat               1248 |
| 6 | aaagaactgg gtcatgatgt gctgaaaccg tatgatggtt gggcaagcta tggtgaaggt    60<br>acaaccggtg gtagcatggc aagtccgcag aatgtttata ccgttaccaa taaaaccgaa    120<br>ctggttcagg cactgggtgg taataatcat accaatcagt ataattccgt gccgaaaatc    180<br>atctatgtga aaggcaccat tgaactgaac gtggatgata taatcagcc ggttggtccg    240<br>gaattctata aagatccgca ttatgatttt gaagcctatc tgaaagagta tgatccgaaa    300<br>aaatgggca aaaaagaagt tagcggtccg ctggaagaag cacgcgcacg tagccagaaa    360<br>aaacagaaag aacgtattgt tgtgaatgtg ggtagcaaca ccagcattat tggtgttggt    420<br>aaagatgcca aaattgtggg tggtggtttc ctgattaaaa acgtggataa tgtgatcatc    480<br>cgcaacatcg aatttgaagc accgctggat tattttccgg aatgggatcc gaccgatggc    540<br>accctgggtg aatggaatag cgaatatgat agcattacca ttgaaggcag ccatcatatt    600<br>tggatcgatc acaataccct taccgatggc gatcatccgg ataaaagcct gggcacctat    660<br>tttggtcgtc cgtttcagca gcatgatggc gcactggata tcaaaaatag cagcgatttt    720<br>atcaccatca gctacaacgt gtttaaagac catgataaag tgaccctgat tggtgcaagc    780<br>gatagccgta tggcagatga aggtcatctg cgtgttaccc tgcatcacaa ttattacaaa    840<br>aatgttaccc agcgtctgcc tcgtgttcgt tttggtcagg ttcatatcta taacaactac    900<br>tatgagttta gcaacctggc cgattatgac tttcagtatg catggggtgt tggtgttgaa    960<br>agcaaaatct atgcccagaa caactatttc agcttcgatt gggatattga tccgagcaaa   1020<br>attatcaaag tttggagcaa aaacgaagaa acatgtatg aaagcggtac gattgttgat   1080<br>ctgccgaatg gtcgtcgtta tattgatctg gttgcaagct ataatgaaag caatacctg    1140<br>cagctgaaaa agaggttgg ttggaaaccg atgttctatc atgttattca tccgaccccg    1200<br>agcgttccgg cactggttaa agcaaaagcc ggtgcaggta atctgcat               1248 |

TABLE 2-continued

Amino acid and nucleotide sequences provided herein

| SEQ ID NO: | Sequence | |
|---|---|---|
| 7 | aaagaactgg gtcatgatgt gctgaaaccg aatgatggtt gggcaagcta tggtgaaggt | 60 |
| | acaaccggtg gtagcgaagc aagtccggat aatgtttata ccgttaccaa taaaagcgaa | 120 |
| | ctggttcagg cactgggtgg taataatcat accaatcagt ataattccac cccgaaaatc | 180 |
| | atctatgtga aaggcaccat tgaactgaac gtggatgata taatcagcc ggttggtccg | 240 |
| | gaatattatg atgatccgca ttatgatttt gaagcctatc tgaaagagta tgatccgaaa | 300 |
| | aaatggggca aaaagaagt tagcggtccg ctggaagaag cacgcgcacg tagccagaaa | 360 |
| | aaacagaaag aacgtattgt tgtgaatgtg ggtagcaaca ccagcattat tggtgttggt | 420 |
| | aaagatgcca aaattgtggg tggtgtttc ctgattaaaa acgtggataa tgtgatcatc | 480 |
| | cgcaacatcg aatttgaagc accggttgat tttttccgg aatgggatcc gaccgatggt | 540 |
| | gaatatggcg aatggaatag cgaatatgat agcattacca tcgaaagcag ccatcatatt | 600 |
| | tggatcgatc acaataccct taccgatggc gatcatccgg ataaaagcct gggcacctat | 660 |
| | tttggtcgtc cgtttcagca gcatgatggc gcactggatta tcaaaaatag cagcgatttt | 720 |
| | atcaccatca gctacaacgt gtttaaagac catgataaag tgagcctgat tggttcaagc | 780 |
| | gatagccgta aaaccgatga aggtcatctg aaagttaccc tgcatcacaa ctattacaaa | 840 |
| | aatgttaccc agcgtctgcc tcgtgttcgt tttggtcagg ttcatatcta taacaactac | 900 |
| | tatgagttta gcaacctggc cgattatgac tttcagtgtc atggggtgt tggtgttgaa | 960 |
| | agcaaaatct atgcccagaa caactatttc agcttcgatt gggatattga cccgagcaaa | 1020 |
| | attatcaaag tttggagcaa aaacgaagaa agcatgtatg aaagcggtac gattgttgat | 1080 |
| | ctgccgaatg tcgtcgtta tattgatctg gttgcaagct ataatgaaag caatacctg | 1140 |
| | cagctgaaaa aagaggttgg ttggaaaccg atgttctatc atgttattca tccgaccccg | 1200 |
| | agcgttccgg cactggttaa agcaaaagcc ggtgcaggta atctgcat | 1248 |
| 8 | atgcgtcgca aactggaaaa atttgttgat agcctgccga ttatggaaac cctgcagccg | 60 |
| | aaaaccaaag gcaaaaacta ttatgaggtg aaaatccaag agtttaaaaa aaactgcac | 120 |
| | cgtgatctgc ctccgaccac cctgtggggt tataatgcac agtttccggg tccgaccatt | 180 |
| | gaagcaaaata gcaatgaacc ggttgaagtg aaatggatta atgagctgcc gaacaaacat | 240 |
| | tttctgccgg ttgattggag catcatgaat aaagatctgc cggaagttcg tcatgttacc | 300 |
| | catctgcatg gtggtcgtac cccgagtgtt agtgatggtt atccggaagc atggtatacg | 360 |
| | aaagattata aagaagtggg cagcttcttc aaagaagagg tttatcgtta tctgaatgaa | 420 |
| | cagcgtgcaa tgatgctgtg gtatcatgat cataccatgg gtattacccg tctgaataac | 480 |
| | tatgcaggtc tggcaggcgc atatatcatt cgtgataaac atgaaaaag cctgaatctg | 540 |
| | cctgaaggcg aatatgaagt tccgctgatt attcaggatc gcacctttaa tgaagatggc | 600 |
| | agcctgtttt atccgaccgg tccggaagat ggcggtgagg atctgccgaa tccgagcatt | 660 |
| | gttccggcat ttctgggtga taccgttctg gttaatggta agtttggcc gtatctggaa | 720 |
| | gttgaaccgc gtaaatatcg ttttcgtatt ctgaatggta gcaacgcccg tagctatcag | 780 |
| | ctgcatctgg atagcaatca agaagtgtat cagattggtt cagatggtgg tctgctggaa | 840 |
| | aaaccggtgc agataacaa aattccgatt gaaagcagcg aacgcattga tgtgattatc | 900 |
| | gattttagcc agtgtgatgg tgatgagatt gtgctgaaaa atgatctggg tccggatgca | 960 |
| | gatgccgaag atgaaaccaa tgaaatcatg aaattcaaag tgagcaaacc gctgaaagag | 1020 |
| | aaagatacca gcgttattcc gaaacgtctg agcaccattc gtagcctgcg taataacaaa | 1080 |
| | attagcaccc atcgtaatct gaaactggtt ggtagcaccg atgatttggg tcgtcctctg | 1140 |
| | ctgctgctga caacaaaaa atgggcagat ccgaccacag aaaaaccgaa agttggcgat | 1200 |
| | accgaagttt ggagctttat taacaccacc gattttgcac atccgatgca tattcatctg | 1260 |
| | atccatttc aggttctgga tcgtcagccg tttgatctgg aacgttataa tcatgatggc | 1320 |
| | accattatct ataccggtcc gcctcgtgca ccggaaccga tgaacgtgg ttggaaagat | 1380 |
| | acagttagcg caccggcagg tcagattacc cgtgttattg gcacctttgc accgtatacc | 1440 |
| | ggtaattatg tttggcattg tcatatcctg gaacacgaag atcacgatat gatgcgtccg | 1500 |
| | atgaaagtta ttgatccgaa acagcgtaaa gataaa | 1536 |

---

The invention claimed is:

1. A method for producing a reducing sugar from a lignocellulosic material, the method comprising:
    pretreating the lignocellulosic material with a pectate lyase (EC 4.2.2.2) at a pH between 9 and 12,
    treating the lignocellulosic material with at least one cellulase or hemicellulase; and
    obtaining at least 80% of the theoretical yield of reducing sugars from the lignocellulosic material;
    wherein the pectate lyase comprises the full length of the amino acid sequence according to SEQ ID NO: 1 or an amino acid sequence at least 89% identical with the full length of SEQ ID NO: 1.

2. The method according to claim 1, wherein the reducing sugar is a fermentable sugar.

3. The method according to claim 1, wherein the lignocellulosic material is selected from the group consisting of corn stover, bioenergy crops, agricultural residues, municipal solid waste, industrial solid waste, yard waste, wood and forestry waste, sugar cane, switchgrass, wheat straw, hay, barley, barley straw, rice straw, grasses, waste paper, sludge from paper manufacture, byproducts from paper manufacture, corn grain, corn cobs, corn husks, grasses, wheat, rice straw, sugar cane bagasse, sorghum, soy, trees, branches, wood chips, and sawdust.

4. The method according to claim 1, wherein the lignocellulosic material is contacted with a laccase (EC 1.10.3.2), simultaneously or sequentially with the pectate lyase, wherein the laccase comprises an amino acid sequence at least 90% identical with the full length of SEP ID NO: 4.

5. The method according to claim 4, wherein the laccase comprises the full length of the amino acid sequence according to SEQ ID NO: 4 or an amino acid sequence at least 95% identical with the full length of SEQ ID NO: 4.

6. The method according to claim 1, wherein the lignocellulosic material is also pretreated with a steam explosion step or ammonia fiber explosion.

7. The method according to claim 1, wherein the pectate lyase was produced by heterologous expression in *Escherichia coli*.

8. The method according to claim 1, wherein the pectate lyase has an amino acid sequence that is at least 93% identical to the full length of the sequence according to SEQ ID NO:1.

9. The method according to claim 1, wherein the pectate lyase has an amino acid sequence that is at least 96% identical to the full length of the sequence according to SEQ ID NO:1.

10. The method according to claim 1, wherein the pectate lyase has an amino acid sequence that is at least 98% identical to the full length of the sequence according to SEQ ID NO:1.

11. The method according to claim 1, wherein the pectate lyase has an amino acid sequence that is at least 99% identical to the full length of the sequence according to SEQ ID NO:1.

12. The method according to claim 4, wherein the laccase comprises an amino acid sequence at least 95% identical with the full length of SEQ ID NO: 4.

* * * * *